(12) United States Patent
Le Hir De Fallois et al.

(10) Patent No.: US 11,773,066 B2
(45) Date of Patent: Oct. 3, 2023

(54) INDAZOLYLCYANOETHYLAMINO COMPOUND, COMPOSITIONS OF SAME, METHOD OF MAKING, AND METHODS OF USING THEREOF

(71) Applicant: BOEHRINGER INGELHEIM ANIMAL HEALTH USA INC., Duluth, GA (US)

(72) Inventors: Loïc Patrick Le Hir De Fallois, Hopewell, NJ (US); Hyoung Ik Lee, Alpharetta, GA (US); Charles Q Meng, Grayson, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 339 days.

(21) Appl. No.: 17/294,761

(22) PCT Filed: Nov. 14, 2019

(86) PCT No.: PCT/US2019/061519
§ 371 (c)(1),
(2) Date: May 18, 2021

(87) PCT Pub. No.: WO2020/112374
PCT Pub. Date: Jun. 4, 2020

(65) Prior Publication Data
US 2022/0017473 A1      Jan. 20, 2022

Related U.S. Application Data

(60) Provisional application No. 62/769,850, filed on Nov. 20, 2018.

(51) Int. Cl.
| | |
|---|---|
| *C07D 231/56* | (2006.01) |
| *A61K 31/366* | (2006.01) |
| *A61K 31/416* | (2006.01) |
| *A61K 31/7048* | (2006.01) |

(52) U.S. Cl.
CPC .......... *C07D 231/56* (2013.01); *A61K 31/366* (2013.01); *A61K 31/416* (2013.01); *A61K 31/7048* (2013.01); *C07B 2200/07* (2013.01)

(58) Field of Classification Search
None
See application file for complete search history.

(56) References Cited

U.S. PATENT DOCUMENTS

| | | |
|---|---|---|
| 8,088,801 B2 | 1/2012 | Soll et al. |
| 8,283,475 B2 | 10/2012 | Soll et al. |
| 8,461,176 B2 | 6/2013 | Soll et al. |

FOREIGN PATENT DOCUMENTS

| | | |
|---|---|---|
| WO | 2008/144275 A1 | 11/2008 |
| WO | 2010/056999 A1 | 5/2010 |

OTHER PUBLICATIONS

Zafrani, Y., Yeffet, D., Sod-Moriah, G., Berliner, A., Amir, D., Marciano, D., . . . & Saphier, S. (2017). Difluoromethyl bioisostere: examining the "lipophilic hydrogen bond donor" concept. Journal of Medicinal Chemistry, 60(2), 797-804. (Year: 2017).*

* cited by examiner

*Primary Examiner* — Dale R Miller
(74) *Attorney, Agent, or Firm* — John Ezcurra

(57) ABSTRACT

The compound of formula I:

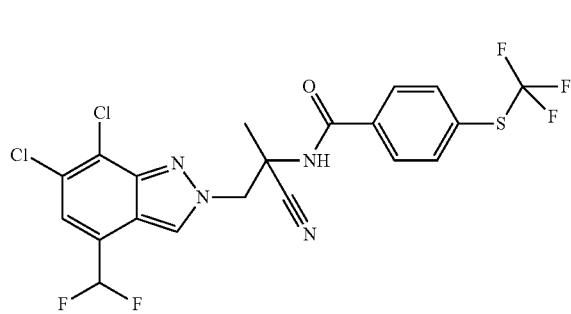

compositions thereof, processes for their preparation, and their uses as pesticides.

19 Claims, No Drawings

INDAZOLYLCYANOETHYLAMINO COMPOUND, COMPOSITIONS OF SAME, METHOD OF MAKING, AND METHODS OF USING THEREOF

CROSS-REFERENCE TO RELATED APPLICATION

This application claims the benefit of priority to U.S. Provisional Application No. 62/769,850, filed Nov. 20, 2018, which is incorporated herein by reference.

FIELD OF THE INVENTION

The present disclosure relates to an indazolylcyanoethylamino compound of formula I or formula II, a composition comprising the compound, a method of making the compound, a use of the compound and a method comprising the compound for treating and/or preventing a parasitic infection in an animal.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

BACKGROUND OF THE INVENTION

The control of parasites, particularly endoparasites, by means of an active ingredient having a cyanoethylamino group has been described by various patents or patent applications including International Patent Publication Nos. WO 2004/024704 (U.S. Pat. No. 7,084,280), WO 2005/044784, WO 2005/121075 and WO 2006/043654 as well as EP 953565 (U.S. Pat. No. 6,239,077) and EP 1445251, all incorporated herein by reference.

In addition, certain indazolylcyanoethylamino compounds having a bicyclic heteroaryl component are known. For example, aryloazol-2-yl-cyanoethylamino compounds are described in PCT Publication Nos. WO 2008/144275 and WO2010/056999, both incorporated herein by reference in their entirety. However, the compound of the present invention has not been specifically described.

SUMMARY OF THE INVENTION

In one embodiment, the present invention provides a compound of formula I:

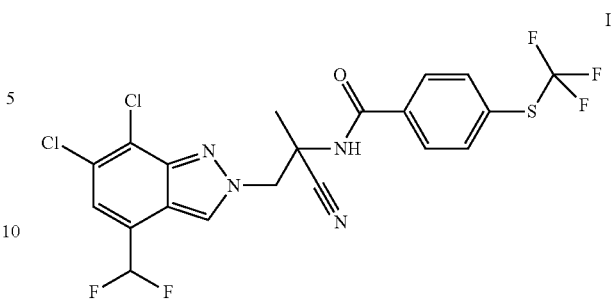

and/or a pharmaceutically acceptable salt thereof and/or an enantiomer thereof.

In another embodiment, the invention provides a compound of formula II:

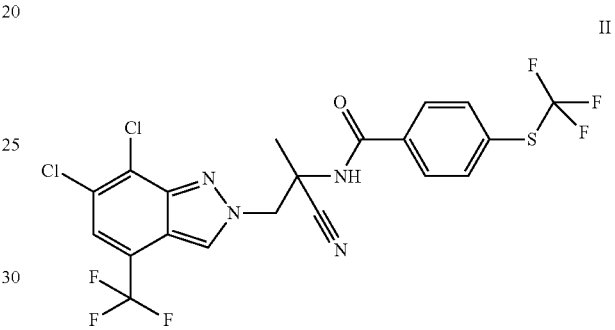

and/or an acceptable salt thereof and/or an enantiomer thereof.

In another embodiment, the invention provides a pesticidal or parasiticidal composition comprising a compound of formula I or a compound of formula II and a pesticidally-acceptable or parasiticidally-acceptable carrier. In some embodiments, the compositions are suitable for oral administration to an animal. In other embodiments, the compositions are in the form for administration by injection. In other embodiments, the compositions are in the form for topical administration to an animal, including pour-on or spot-on formulations.

In another embodiment, the invention provides a method for treating and/or preventing an endoparasitic infection in a mammal which comprises administering an effective amount of a compound of formula I or formula II, or pharmaceutically acceptable salts thereof, or a composition comprising the compound or salt, to an animal in need thereof.

In yet another embodiment, the invention provides for the use of the compound of formula I or formula II, or pharmaceutically acceptable salts thereof, for treating or preventing an endoparasitic infection in an animal. The invention also provides for the use of the compound of formula I or formula II, or salts thereof, in the manufacture of a medicament for the treatment or prevention of an endoparasitic infection in an animal.

The compounds, compositions, methods and uses of the invention are effective for treating animals including mammals, birds and fish. Examples of mammals include, but are not limited to, humans, cattle, sheep, goats, llamas, alpacas, pigs, horses, donkeys, dogs, cats and other livestock or domestic mammals. Examples of birds include turkeys, chickens, ostriches and other livestock or domestic birds.

The use of the compounds of formula I and formula II to protect ruminant animals such as cattle and sheep from endoparasites is particularly useful.

In one embodiment, the methods and uses of the invention are effective against an endoparasitic infection caused by a helminth selected from the group consisting of Anaplocephaela (*Anoplocephala*), *Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

In another embodiment, the methods and uses of the invention is effective against an endoparasitic infection caused by a helminth selected from the group consisting of *Haemonchus contortus, Ostertagia circumcincta, Trichostrongylus axei, Trichostrongylus colubriformis, Cooperia curticei* and *Nematodirus battus*, or combinations thereof.

In another embodiment, the compounds, compositions, methods and uses of the invention are effective against resistant strains of the endoparasites listed in the two previous paragraphs.

In another embodiment, the invention provides a process for the manufacture of a compound of formula I or formula II.

DETAILED DESCRIPTION OF THE INVENTION

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one specific embodiment, the term "about" or "approximately" means within 20%. In another embodiment, the term "about" means within 5% of a given value or range.

Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

The term "animal" is used herein to include all mammals, birds and fish and also include all vertebrate animals, including humans. Animals include, but are not limited to, humans, cats, dogs, cattle, chickens, cows, deer, goats, horses, donkeys, llamas, alpacas, pigs, sheep and yaks. Examples of birds include turkeys, chickens, ostriches and other livestock or domestic birds. It also includes an individual animal in all stages of development, including embryonic and fetal stages.

The term "effective amount" as used herein means a concentration of the active agent in the composition sufficient to elicit the desired biological response to the target parasite(s) after administration of the composition to the animal, as measured by methods known in the art and/or described in the examples herein. In some embodiments, an "effective amount" of the active agent in the composition will provide an efficacy of at least 70% against the target parasite compared to an untreated control. In other embodiments, "an effective amount" of the active agent will provide an efficacy of at least 80%, or at least 85% compared to untreated controls. More typically, "an effective amount" of the active agents will provide an efficacy of at least 90%, at least 93%, at least 95% or at least 97% against the target parasite.

In an embodiment, the present invention includes the compound of formula (I):

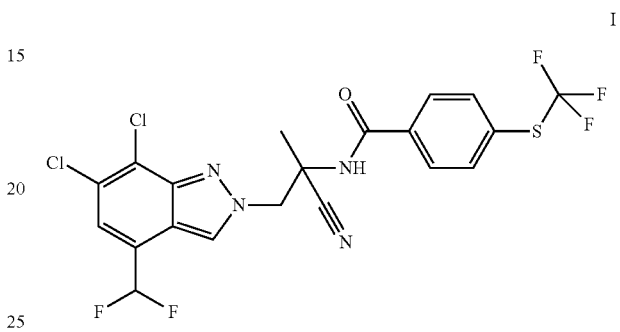

and/or an acceptable salt thereof and/or an enantiomer thereof.

In another embodiment, the present invention provides a compound of formula II:

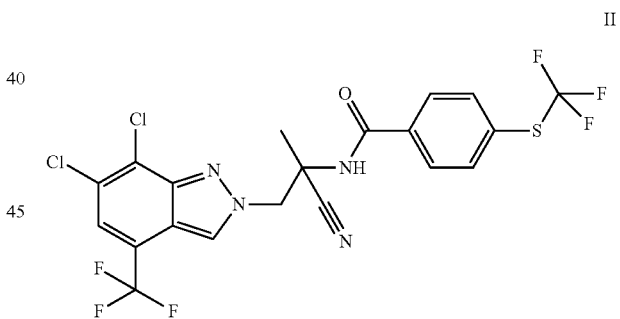

and/or an acceptable salt thereof and/or an enantiomer thereof.

In one embodiment, the compound of formula I or formula II may be enriched in an enantiomer. As defined herein, enriched in an enantiomer means that the compound of formula I or formula II is enriched in the R or S enantiomer relative to the other enantiomer in a ration of at least 80:20 by weight. In other embodiments, the compound of formula I or formula II is enriched in an enantiomer (either R or S) in a ratio of at least 90:10, 95:5 or 97:3 by weight. In yet another embodiment, the compound of formula I or formula II is enriched in an enantiomer in a ratio of at least 98:2 or 99:1 by weight. In an embodiment, the compound of formula I or formula II may be the compound of formula I-R, I-S, II-R and/or II-S, respectively, and/or an acceptable salt thereof:

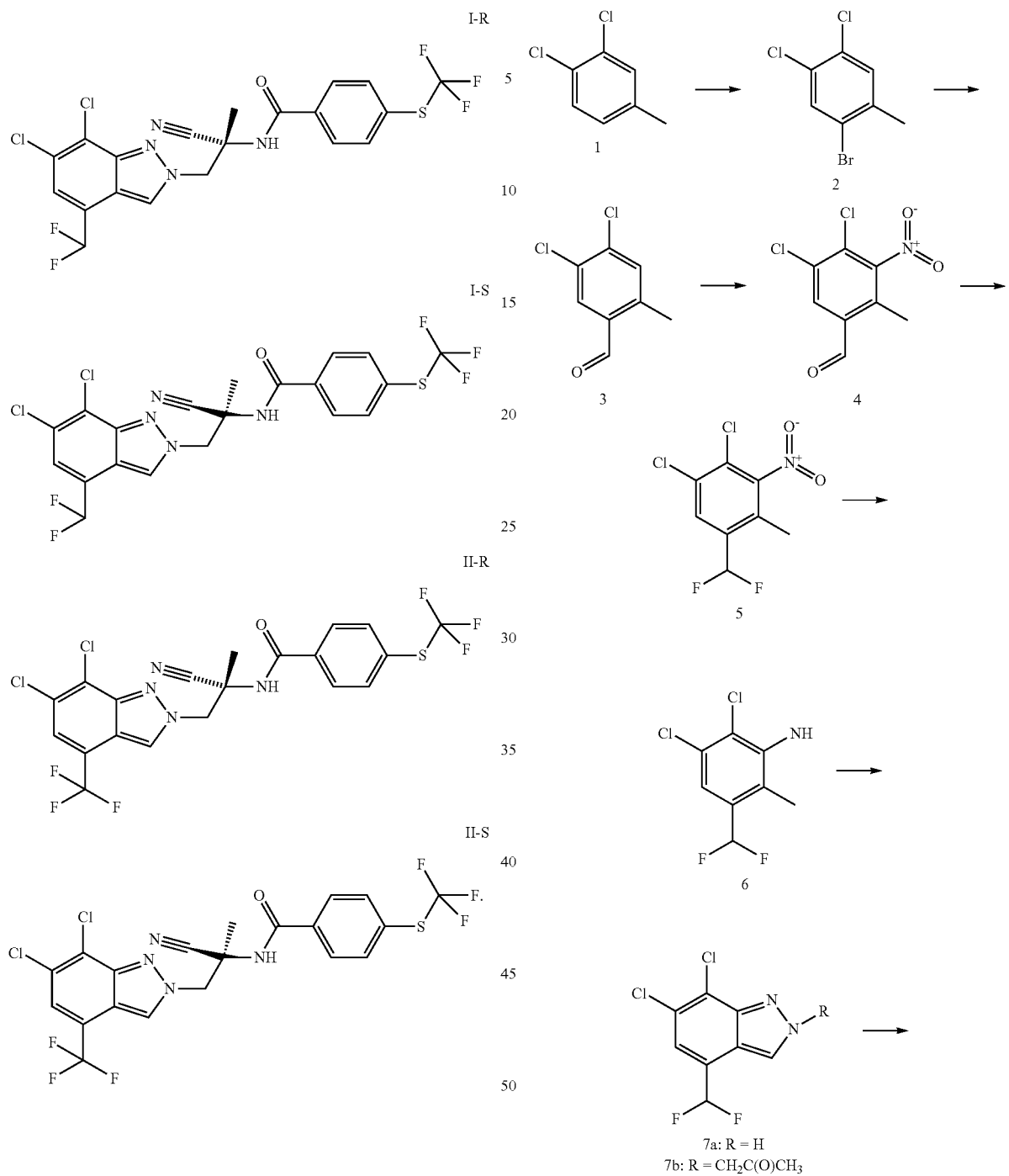

The compounds of formula I and/or formula II and/or a salt and/or an enantiomer thereof are highly active against endoparasites in vitro and in vivo. In particular, it has been found that the compound of formula I exhibits surprisingly potent activity against certain endoparasites, including *Haemonchus contortus*, when compared with compounds having very similar structures and substitution patterns. The improved activity of the compound of formula I is surprising and unexpected.

In an embodiment, the compound of formula (I) may be prepared by the following scheme:

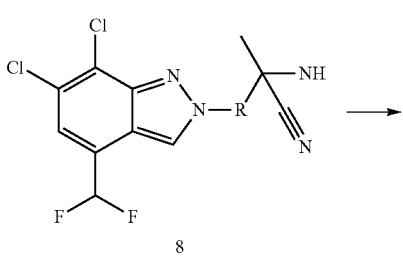

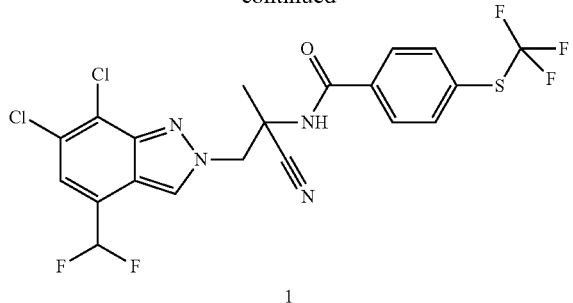

1

The compound of formula 1, commercially available 3,4-dichlorotoluene, may be halogenated, e.g., brominated, according to methods known to those of skill in the art to produce the compound of formula 2. The compound of formula 3 may be prepared by metalation of the C—Br bond of 2 followed by addition of a formylating agent, e.g., N,N-dimethylformamide. The compound of formula 3 may be nitrated according to methods known to those of skill in the art to produce the compound of formula 4. Difluorination of the compound of formula 4, e.g., with a fluorinating agent such as, or BAST, provides the compound of formula 5. Reduction under conditions known to those of skill in the art provides aniline 6. Aniline 6 is then converted to heterocycle 7a by diazotization under standard conditions known to the person of skill in the art. Alkylation with a haloacetone, e.g., chloroacetone, to produce 7b, followed by reaction with cyanide in ammonium chloride provides aminonitrile 8. Reaction of 8 with 4-trifluoromethylthiobenzoyl chloride provides compound I.

Another embodiment of the invention includes parasiticidal compositions which comprise the compound of formula I and/or formula II. The composition of the disclosure can also be in a variety of forms which include, but are not limited to, oral formulations, injectable formulations, and topical, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compound of formula I or II to protect companion animals such as dogs and cats from endoparasites is particularly useful.

Veterinary compositions: The compounds of formula I and formula II and compositions comprising the compounds are useful for the prevention and treatment of parasitic infestations/infections in animals. The compositions of the invention comprise an effective amount of at least one compound of formula I or II, or a veterinarily acceptable salt thereof, in combination with a veterinarily acceptable carrier or diluent and optionally other non-active excipients. The compositions may be in a variety of solid and liquid forms which are suitable for various forms of application or administration to an animal. For example, the veterinary compositions comprising the inventive compounds may be in formulations suitable for oral administration, injectable administration, including subcutaneous and parenteral administration, and topical administration (e.g., spot-on or pour-on), dermal or subdermal administration.

The compositions of the invention may be in a form suitable for oral use (see, e.g., U.S. Pat. No. 4,564,631, which is hereby incorporated by reference in its entirety), dietary supplements, troches, lozenges, chewables including soft chewable compositions, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more sweetening agents, bittering agents, flavoring agents, coloring agents and/or preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral formulations include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example, peanut oil, liquid paraffin, or olive oil.

In one embodiment, the compounds of formula I and II may be administered in chewable tablet compositions or soft chewable compositions such as those described in US 2013/0203692 A1, US 2010/0087492, US 2006/0222684, US 2004/0151759, and U.S. Pat. No. 7,955,632, all incorporated herein by reference. The veterinary compositions may be in the form of a soft chewable formulation ("soft chew") which is palatable and acceptable to the animal. In addition to the active ingredient(s), the soft chews of the invention may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the invention include, but are not limited to, various grades of liquid polyethylene glycol (PEG) including PEG 200, PEG 300, PEG 400 and PEG 540; propylene carbonate; alcohols including ethanol, isopropanol and benzyl alcohol; propylene glycol; triglycerides including, but not limited to, caprylic/capric triglyceride, caprylic/capric/linoleic triglyceride (e.g., Miglyol® 810 and 812), caprylic/capric/succinic triglyceride, propylene glycol dicaprylate/dicaprate, and the like; water, sorbitol solution, glycerol caprylate/caprate and polyglycolized glycerides (Gelucire®), or a combination thereof.

Various fillers known in the art may be used in the soft chewable compositions of the invention. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the invention include, but are not limited to, polyvinylpyrrolidone (e.g., Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g., Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the composition to improve solubility and absorption after ingestion. Surfactants are typically present in a concentration of about 1 to 10% (w/w), more typically about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-$\alpha$2tocopheryl polyethylene glycol 1000 succinate (TPGS), sodium lauryl sulfate, co-polymers of ethylene oxide and propylene oxide (e.g., poloxamers such as Lutrol® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (Lauroglycol®); glyceride esters including glycerol caprylate/caprate (Capmul® MCM), polyglycolized glycerides (Gelucire®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate), and the like.

The inventive formulations may contain other inert ingredients such as antioxidants, preservatives, or pH stabilizers. These compounds are well known in the formulation art. Antioxidants may be added to the compositions of the invention to inhibit degradation of the active agents. Suitable antioxidants include, but are not limited to, alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The compositions of the invention may also include one or more lubricants and/or processing aids. In some cases, the lubricant/processing aid may also behave as a solvent, and accordingly, some of the components of the inventive compositions may have dual functions. Lubricants/processing aids include, but are not limited to, polyethylene glycols of various molecular weight ranges including PEG 3350 (Dow Chemical) and PEG 4000, corn oil, mineral oil, hydrogenated vegetable oils (Stereotex or Lubritab), peanut oil and/or castor oil.

Many flavoring agents may be used in the compositions of the invention to improve the palatability of the oral veterinary formulations. Preferred flavoring agents are those that are not derived from animal sources. In various embodiments, flavoring components derived from fruit, meat (including, but not limited to, pork, beef, chicken, fish, poultry, and the like), vegetable, cheese, bacon, cheese-bacon and/or artificial flavorings may be used. A flavoring component is typically chosen based upon consideration related to the animal that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used, such as braised beef flavor, artificial powdered beef flavor, roast beef flavor and corned beef flavor among others.

In another embodiment of the invention, the active composition may be administered via a drench, and may be administered either topically or orally. Drench formulations are those in which the liquid-containing compositions of the invention are administered to the mouth or throat of the animal, or poured onto the skin or coat of the animal. The drench formulations include a compound of formula I or formula II dissolved in an acceptable solvent, suspended in an acceptable medium or an emulsion comprising the compound. Acceptable carriers will be known to those of skill in the art and include, but are not limited to, water, oils, certain liquid polymers such as polyethylene glycols (PEGs). In one embodiment, the drench formulations of the invention comprise a liquid polyethylene glycol such as PEG 300 and/or PEG 400.

The compositions of the invention may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of microdroplets of the aqueous phase in the oily phase or conversely of microdroplets of the oily phase in the aqueous phase. The size of these microdroplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropylene glycol monomethyl ether, polyglycolyzed $C_8$-$C_{10}$ glycerides or polyglyceryl-6 dioleate. In addition to these surfactants, the co-surfactants may include short-chain alcohols, such as ethanol and propanol.

Some compounds are common to the three components discussed above, i.e., aqueous phase, surfactant and co-surfactant. However, it is well within the skill level of the practitioner to use different compounds for each component of the same formulation. In one embodiment for the amount of surfactant/co-surfactant, the co-surfactant to surfactant ratio will be from about 1/7 to about 1/2. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment, the location may be between the shoulders. In another embodiment it may be a stripe, e.g., a stripe from head to tail of the animal.

Pour-on formulations are described in U.S. Pat. No. 6,010,710, also incorporated herein by reference. Pour-on formulations may be advantageously oily, and generally comprise a diluent or vehicle and also a solvent (e.g., an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethyl sulfoxide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g., N-methylpyrrolidone), propylene carbonate, diethylene glycol monoethyl ether, ethylene glycol, triacetin, $C_1$-$C_{10}$ esters of carboxylic acids such as butyl or octyl acetate, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the formulations may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, anionic surfactants such as alkaline stearates, sodium, potassium or ammonium stearates; calcium stearate, triethanolamine stearate; sodium abietate; alkyl sulphates (e.g., sodium lauryl sulphate and sodium cetyl sulphate); sodium dodecylbenzenesulphonate, sodium dioctylsulphosuccinate; fatty acids (e.g., those derived from coconut oil), cationic surfactants include water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (a) amine salts of formula $N^+HR'R''R''$ in which the radicals R are optionally hydroxylated hydrocarbon radicals; octadecylamine hydrochloride is among the cationic surfactants which can be used, (b) nonionic surfactants such as sorbitan esters, which are optionally polyoxyethylenated (e.g., polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (c) amphoteric surfactants such as the substituted lauryl compounds of betaine; or (d) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the formulation. In other embodiments, the amount of crystallization inhibitor in the inventive formulations may be about 1% to about 30%, about 5% to about 20%, about 1% to about 15%, or about 1% to about 10% (w/w). The type of crystallization inhibitor used in the inventive formulations is not limited as long as it functions to inhibit crystallization of the active or inactive agents from the formulation. For example, in certain embodiments of the invention, a solvent or co-solvent of the formulation may also function as a crystallization inhibitor if it sufficiently inhibits the formation of crystals from forming over time when the formulation is administered.

Crystallization inhibitors which are useful for the invention include, but are not limited to: polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

anionic surfactants, such as alkaline stearates (e.g., sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g., coconut oil);

cationic surfactants, such as water-soluble quaternary ammonium salts of formula $N'R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;

amine salts of formula $N^+HR'R''R'''$, in which the R radicals are identical or different optionally hydroxylated hydrocarbon radicals; octadecylamine hydrochloride is one of the cationic surfactants which can be used;

non-ionic surfactants, such as optionally polyoxyethylenated esters of sorbitan, e.g., Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

amphoteric surfactants, such as substituted lauryl compounds of betaine;

a mixture of at least two of the compounds listed in (a)-(f) above; or an organic solvent or mixture of solvents which inhibit the formation of crystals or amorphous solid after the formulation is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(s) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the formulation.

In some embodiments, one or more of the organic solvent(s) may have a boiling point of below about 100° C., or below about 80° C. In other embodiments, the organic solvent(s) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The formulation may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type, which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than 10 crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of at least two compounds with antioxidant properties.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the formulation applied will depend on the type of animal and the size of the animal as well as the strength of the formulation and the potency of the active agents. In one embodiment, an amount of about 0.1 to about 20 ml of the formulation may be applied to the animal. In other embodiment for the volume, the volume may be about 0.1 to about 10 ml, about 0.1 to about 5 ml, about 0.5 ml to about 10 ml, or about 0.3 to about 3 ml.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

The liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the compound of formula I or formula II may be present in the formulation at a concentration of about 0.05 to about 10% weight/volume. In one embodiment, the compound is present in a concentration of about 2 to about 5% (w/v). In another embodiment, the compound is present in a concentration of about 3 to about 6% (w/v). In another embodiment of the invention, the active agent may be present in the formulation as a concentration from about 0.1 to about 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

In one embodiment, the composition comprises a compound of formula I or formula II that is substantially enriched in an enantiomer. The term "substantially enriched" is meant wherein the weight:weight ratio is at least about 1.5:1 or higher in favor of the desired enantiomer. In another embodiment, the extended release injectable compositions comprise a compound of formula I or formula II, that is substantially enriched in the (S)-enantiomer. In another embodiment, the extended release injectable compositions comprise a compound of formula I or formula II that is substantially enriched in the (R)-enantiomer.

In another embodiment, the compositions comprise a compound of formula I or formula II, that is enriched in the (S)-enantiomer in a weight:weight ratio of at least about 2:1, (S) to (R), or greater. In yet another embodiment, the compositions comprise a compound of formula I or formula II that is enriched in the (S)-enantiomer in a weight:weight ratio of at least about 5:1, (S) to (R), or greater. In still another embodiment, the compositions of the invention comprise a compound of formula I or formula II, that is enriched in the (S)-enantiomer in a weight:weight ratio of at least about 10:1, (S) to (R), or greater. In still another embodiment, the compositions comprise a compound of formula I or formula II, that is essentially the pure (S)-enantiomer.

In another embodiment, the compositions comprise a compound of formula I or formula II, that is enriched in the (R)-enantiomer in a weight:weight ratio is at least approximately 2:1, (R) to (S), or greater. In yet another embodiment, the compositions of the invention comprise a compound of formula I or formula II, that is enriched in the (R)-enantiomer in a weight:weight ratio of at least about 5:1, (R) to (S), or greater. In still another embodiment, the compositions of the invention comprise a compound of formula I or formula II, that is enriched in the (R)-enantiomer in a weight:weight ratio of at least about 10:1, (R) to (S), or greater. In still another embodiment, the compositions of the invention comprise a compound of formula I or formula II that is essentially the pure R-enantiomer.

Veterinary Methods and Uses

Another embodiment of the disclosure is directed toward a method of treating endoparasiticidal infection in a mammal in need thereof which comprises administering an effective amount of the compound of the disclosure.

In one embodiment for treating endoparasiticidal infection is that the helminth is selected from the group consisting of but not limited to Anaplocephaela (*Anoplocephala*), *Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

In another embodiment of the disclosure, the helminth is *Haemonchus contortus, Ostertagia circumcincta, Trichostrongylus axei, Trichostrongylus colubriformis, Cooperia curticei, Nematodirus battus* and combinations thereof.

In one embodiment, resistant strains of the organisms above may be controlled according to the disclosure. In an embodiment, the methods and uses of the invention are effective against endoparasites that are not effectively controlled by macrocyclic lactones such as avermectins and milbemycins. In another embodiment, the methods and uses of the invention are effective against endoparasites that are resistant to benzimidazole active agents.

Another embodiment of the disclosure is directed toward a method of treating ectoparasiticidal infection in a mammal in need thereof, which comprises administering an effective amount of the compound of the disclosure.

In one embodiment for treating ectoparasiticidal infection, the infected is selected from the group consisting of but not limited to fleas, ticks, mites, mosquitoes, flies, lice, blowfly and combinations thereof.

In another embodiment, the compositions comprising formula I and/or II compounds may also include other veterinary therapeutic agents. Veterinary pharmaceutical agents that may be included in the compositions of the invention are well-known in the art (see e.g., *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdate, amoxicillin, clavulanate potassium, amphotericin B deoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, auranofin, aurothioglucose, azaperone, azathioprine, azithromycin, baclofen, barbiturates, benazepril, betamethasone, bethanechol chloride, bisacodyl, bismuth sub salicylate, bleomycin sulfate, boldenone undecylenate, bromides, bromocriptine mesylate, budesonide, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftriaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, *Propionibacterium acnes* injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodium thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles may be included in the veterinary compositions of the invention. Arylpyrazoles are known in the art and are suitable for combination with the compounds of formula I or formula II in the compositions of the invention. Examples of such arylpyrazole compounds include but are not limited to those described in U.S. Pat. Nos. 6,001,384; 6,010,710; 6,083,519; 6,096,329; 6,174,540; 6,685,954, 6,998,131 and 7,759,381 (all of which are incorporated herein by reference). A particularly preferred arylpyrazole active agent is fipronil.

In another embodiment of the invention, one or more macrocyclic lactones, which act as an acaricide, an anthelmintic agent and/or an insecticide, can be included in the compositions of the invention in combination with the compounds of formula I or formula II. For the avoidance of doubt, the term "macrocyclic lactone" as used herein includes both naturally occurring and synthetic or semisynthetic avermectin and milbemycin compounds. It has been found that combinations of a compound of formula I or formula II with an avermectin or milbemycin active agent are particularly effective in controlling endoparasites that are difficult to control with avermectins or milbemycin alone.

The macrocyclic lactones that may be used in the compositions of the invention include, but are not limited to, the naturally produced avermectins (e.g., including the components designated as $A_1a$, $A_1b$, $A_2a$, $A_2b$, $B_1a$, $B_1b$, $B_2a$ and $B_2b$) and milbemycin compounds, semisynthetic avermectins and milbemycins, avermectin monosaccharide compounds and avermectin aglycone compounds. Examples of macrocyclic lactone compounds that may be used in the compositions include, but are not limited to, abamectin, dimadectin, doramectin, emamectin, eprinomectin, ivermectin, latidectin, lepimectin, selamectin, ML-1,694,554 and milbemycins including, but not limited to, milbemectin, milbemycin D, milbemycin $A_3$, milbemycin $A_4$, milbemycin oxime, moxidectin and nemadectin. Also included are the 5-oxo and 5-oxime derivatives of said avermectins and milbemycins.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569 (both incorporated herein by reference). Mention is also made of U.S. Pat. Nos. 4,468,390, 5,824,653, EP 0 007 812 A1, U.K. Patent Specification 1 390 336, EP 0 002 916, and New Zealand Patent No. 237 086 (all incorporated by reference), inter alia. Naturally occurring milbemycins are described in U.S. Pat. No. 3,950,360, which is incorporated herein by reference, as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054 (all incorporated by reference).

In another embodiment, compound I or compound II may be combined with a class of compounds known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment, the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In another embodiment, the IGR compound is a chitin synthesis inhibitor. Chitin synthesis inhibitors include chlorfluazuron, cyromazine, diflubenzuron, fluazuron, flucycloxuron, flufenoxuron, hexaflumuron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be combined with compound I or compound II. These include pyrethrins (which include cinerin I, cinerin II, jasmolin I, jasmolin II, pyrethrin I, pyrethrin II and mixtures thereof) and pyrethroids (including permethrin cyhalothrin, cypermethrin, deltamethrin, fenvalerate, flucythrinate), and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, compound I or compound II may be combined with one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, compound I or compound II may be combined with an imidazothiazole compounds including, but not limited to, tetramisole, levamisole and butamisole. In still other embodiments, the isoxazoline compounds of the invention may be combined with tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, compound I or compound II may be combined with the antinematodal compounds phenothiazine and piperazine as the neutral compound, or in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, compound I or compound II may be combined with antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously combined with compound I or compound II including, but not limited to, arecoline in various salt forms, bunamidine, niclosamide, nitroscanate, paromomycin and paromomycin II.

In yet other embodiments, compound I or compound II may be combined with other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

In another embodiment, compound I or compound II may be combined with pyrethroid active agents including, but not limited to, permethrin, deltamethrin, cypermethrin, cyphenothrin, etofenprox, fenvalerate and cyfluthrin.

Another antiparasitic agent that can be combined with compound I or compound II includes a biologically active peptide or protein including, but not limited to, depsipeptides, which act at the neuromuscular junction by stimulating presynaptic receptors belonging to the secretin receptor family resulting in the paralysis and death of parasites. In one embodiment, the depsipeptide is emodepside (see Willson et al., *Parasitology*, January 2003, 126(Pt 1):79-86).

In another embodiment, compound I or compound II may be combined with an active agent from the neonicotinoid class of pesticides. The neonicotinoids bind and inhibit insect specific nicotinic acetylcholine receptors. In one embodiment, the neonicotinoid insecticidal agent is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060 (incorporated herein by reference).

In another embodiment, the neonicotinoid active agent is nitenpyram. Nitenpyram is the active ingredient in the oral product CAPSTAR™ Tablets sold by Novartis Animal Health.

Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day.

In certain embodiments, an insecticidal agent that can be combined with compound I or compound II is a semicarbazone, such as metaflumizone.

In another embodiment, compound I or compound II may advantageously be combined with an isoxazoline compound known in the art. The isoxazoline active agents are systemically-acting active agents that are highly effective against ectoparasites. These active agents are described in U.S. Pat. Nos. 7,964,204, 8,410,153, US 2011/0152312, US 2010/0254960 A1, US2011/0159107, US2012/0309620, US2012/0030841, US2010/0069247, WO 2007/125984, WO 2012/086462, U.S. Pat. No. 8,318,757, US 2011/0144349, U.S. Pat. No. 8,053,452; US 2010/0137612, US 2010/0254959, US 2011/152081, WO 2012/089623, WO 2012/089622, U.S. Pat. Nos. 8,119,671; 7,947,715; WO 2102/120135, WO 2012/107533, WO 2011/157748, US 2011/0245274, US 2011/0245239, US 2012/0232026, US 2012/0077765, US 2012/0035122, US 2011/0251247, WO 2011/154433, WO 2011/154434, US 2012/0238517, US 2011/0166193, WO 2011/104088, WO 2011/104087, WO 2011/104089, US 2012/015946, US 2009/0143410, WO 2007/123855 A2, US 2011/0118212, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1, U.S. Pat. Nos. 7,897,630, 7,951,828 and 7,662,972, all of which are incorporated herein by reference in their entirety.

In another embodiment of the invention, nodulisporic acid and its derivatives (a class of known acaricidal, anthelmintic, anti-parasitic and insecticidal agents) may be combined with compound I or compound II. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety.

In another embodiment, anthelmintic compounds of the amino acetonitrile class (AAD) of compounds such as monepantel (Zolvix), and the like, may be combined with compound I or compound II. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The compounds of the invention may also be combined with another aryloazol-2-yl cyanoethylamino compounds such as those described in U.S. Pat. No. 8,088,801 to Soll et al., which is incorporated herein by reference, and thioamide derivatives of these compounds, as described in U.S. Pat. No. 7,964,621, also incorporated herein by reference.

Compound I or compound II may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In another embodiment of the invention, compound I or compound II may be combined with a spinosyn active agent produced by the soil actinomycete *Saccharopolyspora spinosa* (see, for example Salgado V. L. and Sparks T. C., "The Spinosyns: Chemistry, Biochemistry, Mode of Action, and Resistance," in Comprehensive Molecular Insect Science, vol. 6, pp. 137-173, 2005) or a semi-synthetic spinosoid active agent. The spinosyns are typically referred to as factors or components A, B, C, D, E, F, G, H, J, K, L, M, N, O, P, Q, R, S, T, U, V, W, or Y, and any of these components, or a combination thereof, may be used in the compositions of the invention. The spinosyn compound may be a 5,6,5-tricylic ring system, fused to a 12-membered macro cyclic lactone, a neutral sugar (rhamnose), and an amino sugar (forosamine). These and other natural spinosyn compounds, including 21-butenyl spinosyn produced by *Saccharopolyspora pagona*, which may be used in the compositions of the invention, may be produced via fermentation by conventional techniques known in the art. Other spinosyn compounds that may be used in the compositions of the invention are disclosed in U.S. Pat. Nos. 5,496,931; 5,670,364; 5,591,606; 5,571,901; 5,202,242; 5,767,253; 5,840,861; 5,670,486; 5,631,155 and 6,001,981, all incorporated by reference herein in their entirety. The spinosyn compounds may include, but are not limited to, spinosyn A, spinosyn D, spinosad, spinetoram, or combinations thereof. Spinosad is a combination of spinosyn A and spinosyn D, and spinetoram is a combination of 3'-ethoxy-5,6-dihydro spinosyn J and 3'-ethoxy spinosyn L.

In general, the additional active agent is included in the composition in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

Example 1: Preparation of Compound 2, 2-bromo-4,5-dichlorotoluene 3,4-Dichlorotoluene (100 g, 1 equivalent (eq.)) and iron tribromide (55.1 g) were added to 500 mL dichloromethane and cooled to about −5° C. Bromine (99.2 g) was diluted in 100 mL (1 volume (vol.)) dichloromethane and added dropwise to the mixture and the resulting mixture was stirred at about −5° C. The reaction mixture was treated with 12.5% aqueous NaHSO$_3$ (500 mL) at 20° C. and stirred for 30 min. The two phases were allowed to separate and the separated organic layer was washed with saturated aqueous NaHCO$_3$ (600 mL, 6 vol.), brine (500 mL, 5 vol.), and then concentrated under vacuum to about 4-5 vol. Methanol was added to double the volume and the resulting solid filtered, washed with methanol, and dried, to provide 120 g of compound 2 in a purity of 99.7%.

Example 2: Preparation of Compound 3, 2-formyl-3,4-dichlorotoluene

N-Butyllithium (31.2 mL, 2.4 M, 2.0 eq.) was added to anhydrous tetrahydrofuran (20 mL) at about −40 to −50° C. under nitrogen gas. The resulting solution was cooled to about −70° C. Compound 2 was (10 g, 1 eq.) added dropwise as a solution in anhydrous tetrahydrofuran (20 mL) and stirred for 2 hours at about −70° C. to about −80° C. N,N-dimethylformamide (9.1 g, 3 eq) was added and the temperature allowed to warm to about 10° C. Afterwards, aqueous hydrochloric acid (64 mL, 2.6 M) was added and isopropyl acetate (30 mL) added. The organic layer was separated, washed twice with brine (50 mL) and the volume reduced under vacuum at ≤about 40° C. N-heptane was added to triple the volume and then concentrated under vacuum, and then repeated 3 times until the content of THF and isopropyl acetate was determined to be less than 3% by weight. The mixture was stirred for 2 hours at about −5° C. to 0° C., the resulting precipitate filtered and washed with n-Heptane. Compound 3 (6.1 g, 99.7% purity) was obtained as an off-white solid.

Example 3: Preparation of Compound 4, 3,4-dichloro-5-formyl-2-nitrotoluene

Compound 3 (37.8 g, 1 eq.) was added to concentrated sulfuric acid (189 mL, 5 vol.) in portions at −5° C. to 0° C. Fuming nitric acid (25 mL, 2.8 eq.) was added dropwise to the reaction mixture over 15 min and the reaction maintained at −5° C. to 0° C. for 3 hours. Ice water (1 L) was added and the resulting mixture stirred for 2 hours and allowed to rise to ambient temperature. The resulting solid was collected and rinsed with water (12 ml, 3 vol.) twice. The resulting filter cake was treated with saturated aqueous NaHCO$_3$ solution (120 mL) and the resulting solid was filtered to provide 43 g of crude Compound 4 (92.7% purity).

Example 4: Preparation of Compound 5, 3,4-dichloro-5-difluoromethyl-2-nitrotoluene Compound 4 (100 g, 1 eq.) was added to a liter (10 vol.) of dichloromethane and the resulting solution cooled to about 0° C. Bis(2-methoxyethyl)aminosulfurtrifluoride ("BAST", 113.4 g, 1.2 eq.) was added dropwise to the mixture and stirred at about 0° C. Water (400 mL) was added at about 5° C., and the mixture adjusted to pH 7-8 using 15% Na$_2$CO$_3$ solution (about 600 mL). The organic phase was separated and washed with brine (500 mL), concentrated under vacuum to about 3 vol. The resulting residue was mixed with n-heptane (3 vol.) and again concentrated under vacuum. The mixture was stirred for 2 hours at about 0° C. and the solid collected by filtration. The resulting filter cake was washed with n-heptane (100 mL×2) and dried to provide Compound 5 (86 g, 90.1% purity) as a light yellow solid.

Example 5: Preparation of Compound 6, 2,3-dichloro-5-difluoromethyl-6-methylaniline Compound 5 (50 g, 1 eq.) was added to methanol (250 mL, 5 vol.) and palladium on carbon (5 g, 50% in water, 0.10 w/w) added. The reaction mixture was subjected to hydrogen gas at 10 atm at 40-45° C. The reaction was depressurized and the mixture filtered through diatomaceous earth and the filtrate concentrated at 40±5° C. to about 2-3 volumes. Ethyl acetate (3 vol.) was added to the mixture and the resulting mixture concentrated under vacuum at less than 45° C. to about 2-3 volumes. N-heptane (3 vol.) was added to the resulting residue and then the mixture was concentrated under vacuum at less than 45° C. to about 2-3 vol. The n-heptane mixture was stirred for 2 h at about −5 to 0° C., and the resulting precipitate collected, washed with heptane (2×50 mL) to provide Compound 6 (35.6 g, 95.5% purity) as a yellow solid.

Example 6: Preparation of Compound 7a

Glacial acetic acid (3.1 L, 8 vol.) and Compound 6 (385 g, 1 eq.) were mixed and stirred for 30 min, and the resulting mixture cooled to about 0°-10° C. A solution of sodium nitrite (130 g, 1.1 eq.) in 65 mL of water was added in portions in order to maintain the temperature at about 0°-10° C. The mixture was poured into 20 L of ice water in portions to maintain the temperature at about 0°-15° C. The resulting precipitate was collected, washed with water (2 L), heptane (1.2 L) and dried under vacuum to provide a crude product. The crude product was slurried in heptane, re-filtered, and dried, to obtain Compound 7a, (327 g, 95.8% purity).

Example 7: Preparation of Compound 7b

Compound 7a (800 g, 1 eq.) was added to dichloromethane (32 L). Sodium Carbonate (716 g, 2 eq.) in water (8 L) was added, followed by tetrabutylammonium bromide (217 g). The mixture was cooled to 0-5° C., and chloroacetone (375 g, 1.2 eq.) was added. The mixture was warmed to 15-20° C. and stirred 24 hours. The organic layer was separated, washed with water (4 L, 5 vol.) and brine (4 L), and concentrated under vacuum at less than 40° C. The resulting liquid was heated to 35-40° C. and stirred for one hour, then cooled to 0-5° C. and stirred for 2 hours. The resulting precipitate was collected and washed with a 1:1 v/v mixture of dichloromethane: n-heptane (1.6 L total) and dried to obtain Compound 7b as a brown solid (497 g, 97.9% purity).

Example 8: Preparation of Compound 8

Compound 7b (2.0 kg, 1 eq.) was mixed with N,N-dimethylformamide (10 L, 5 vol.), and ammonium chloride (730 g, 2 eq.) added to the mixture. Ammonium hydroxide (4.88 L, 7 M, 5 eq.) was added, and the resulting mixture cooled to 10-15° C. Trimethylsilyl cyanide (1.36 kg, 2 eq.) was added while maintaining the temperature at about 10-15° C. The reaction was heated to 40-45° C. for 24 hours, then diluted into water (40 L, 20 vol.), and the resulting mixture stirred for 2 hours. The resulting precipitate was collected and washed with water (3×2 L), and dried at 50-55° C. for 16 hours to provide Compound 8 as a light yellow solid (2.05 kg, 97.4% purity).

Example 9: Preparation of Compound I

Compound 8 (3.5 kg, 1 eq.) was added to tetrahydrofuran (35 L, 10 vol.) and cooled to 0-5° C. Triethylamine (1.67 kg, 1.5 eq.) was added, followed by 4-(trifluoromethylthio) benzoyl chloride (2.80 kg, 1.05 eq.) while maintaining the temperature at 0-5° C. The reaction mixture was stirred for 2 hours, and concentrated at 40° C. to 2-3 volumes. Dichloromethane (17.5 L, 5 vol.) was added and the mixture concentrated under vacuum at about 40° C. or less to 2-3 volumes. Dichloromethane (52.5 L) was added and the organic phase washed with aqueous hydrochloric acid (17.5 L, 0.5 M), saturated aqueous NaHCO$_3$ solution (17.5 L), water (17.5 L) and brine (17.5 L). The organic phase was concentrated at 40° C. to about 2-3 volumes, then cooled to 0-5° C. and stirred for 2 hours. The resulting precipitate was collected and the filtrate washed with dichloromethane (3×3.5 L). The crude product (4.66 kg) was added to dichloromethane (7 L, 2 vol.), the mixture heated to 40° C., and stirred for 2 hours. The mixture was cooled to 0-5° C. and stirred for 2 hours. The resulting solid was collected and washed with dichloromethane (7 L) and dried to obtain compound I as a light brown solid (4.15 kg, 99.7% purity, 72.3% yield). Purification of Compound I to 99.9% purity was obtained by recrystallization in methanol.

Example 10: Three Compounds from Patent Publication No. WO2010/056999 (999 App)

Compound I, and Compound II were tested in vitro against *Haemonchus contortus* larvae to determine the minimum concentration at which the compounds inhibited the motility of the larvae by 90% (MIC$_{90}$). The following procedure was used for the study: Twenty L1 *Haemonchus contortus* larvae were added to wells of a microtitre plate containing a nutrient medium and the test compound in DMSO. The microtitre plate was held at 27° C. and 97% Relative humidity for a 4 day period. Under these conditions the added larvae develop to the L3 stage. The efficacy of a compound is determined based on the motility of the resulting L3 larvae and compared to the motility of control wells treated with DMSO only.

The MIC$_{90}$ of each compound is shown below in Table 1:

TABLE 1

| Compound | MIC$_{90}$ (ppm) |
| --- | --- |
| I | 0.0003 |
| '999 App, 2.038 | 0.0024 |
| '999 App, 2.041 | 0.0024 |
| '999 App, 2.049 | 0.0012 |
| II | 0.0012 |

Compound 2.038 is

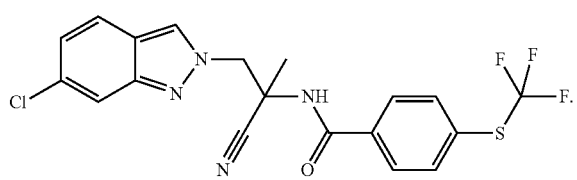 [SMILES: CC(C#N)(Cn1cc2ccc(Cl)cc2n1)NC(=O)c1ccc(SC(F)(F)F)cc1]

Compound 2.041 is

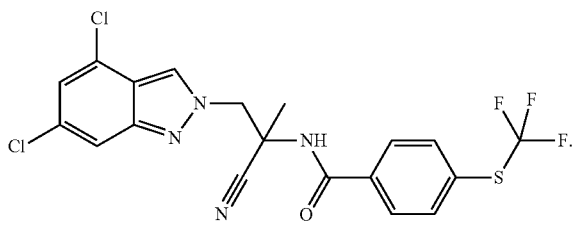 [SMILES: CC(C#N)(Cn1cc2c(Cl)cc(Cl)cc2n1)NC(=O)c1ccc(SC(F)(F)F)cc1]

Compound 2.049 is

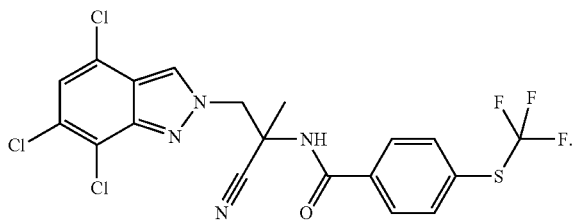 [SMILES: CC(C#N)(Cn1cc2c(Cl)cc(Cl)c(Cl)c2n1)NC(=O)c1ccc(SC(F)(F)F)cc1]

Example 11: In Vivo Efficacy of Compound I Alone and in Combination with an Avermectin The efficacy of Compound I against parasitic gastrointestinal nematodes in cattle when administered orally as an oral solution was studied. Thirty male castrate dairy calves of approximately 8 to 12 weeks of age were experimentally infected with parasitic nematodes. The calves were inoculated with *Haemonchus placei* and *Ostertagia ostertagi* on Day −33 and with *Cooperia punctata* and *Cooperia oncophora* on Day −21. Calves were allocated to one of the six treatment groups. Calves in Treatment Group 1 were not treated. Calves in Treatment Groups 2-6 were treated on Day 0 as outlined in the Table 2 below with a formulation containing 5% (w/v) of Compound I in a carrier comprising 50% (v/v) PEG 400 with the remainder (QS to 130 mL0 PEG 300.

TABLE 2

| Treatment Group | Active Agent | Dose |
| --- | --- | --- |
| 1 | Not treated | NA |
| 2 | Compound I | 2 mg/kg |

TABLE 2-continued

| Treatment Group | Active Agent | Dose |
| --- | --- | --- |
| 3 | eprinomectin | 0.075 mg/kg |
| 4 | ivermectin | 0.150 mg/kg |
| 5 | Compound I + eprinomectin | 2 mg/kg + 0.075 mg/kg |
| 6 | Compound I + ivermectin | 2 mg/kg + 0.150 mg/kg |

All calves were euthanized on Day 16 and the abomasum and small intestine were recovered from each calf and processed for parasite recovery. All five calves in the untreated control group harbored adequate infections of *H. placei*, *O. ostertagi*, *C. punctate* and *C. oncophora*. The efficacy of each treatment group relative to the control group is shown in Table 3 below:

| | % Reduction in Worm Counts | | | | | |
| --- | --- | --- | --- | --- | --- | --- |
| Treatment Group | H. placei Adults | O. ostertagi Males | O. ostertagi Females | C. punctata Males | C. oncophora Males | Cooperia spp. Females |
| Group 2 | 100.0 | 96.3 | 96.4 | 100.0 | 83.0 | 90.9 |
| Group 3 | 98.9 | 95.7 | 99.4 | 94.7 | 0 | 55.8 |
| Group 4 | 82 | 75 | 81 | 91 | 0 | 46 |
| Group 5 | 100 | 96.3 | 99.2 | 99.9 | 87.9 | 90.9 |
| Group 6 | 100.0 | 98.9 | 98.6 | 99.9 | 98.7 | 90.4 |

As shown in Table 3, Compound I was significantly more effective against *C. oncophora* males and *Cooperia* spp. female worms compared with eprinomectin (Group 3) or ivermectin (Group 4). In addition, although ivermectin alone was not effective against *C. oncophora* male worms, the combination of Compound I and ivermectin provided almost 100% efficacy. These results demonstrate the surprising efficacy of Compound I against gastrointestinal nematodes, including those that are less susceptible to treatment with avermectins. The efficacy demonstrated by Compound I against nematode strains that are not susceptible to macrocyclic lactone therapy is surprising and unexpected. In addition, the efficacy demonstrated by a combination of Compound I and a macrocyclic lactone against these nematodes is also surprising and unexpected.

We claim:
1. A compound of formula I:

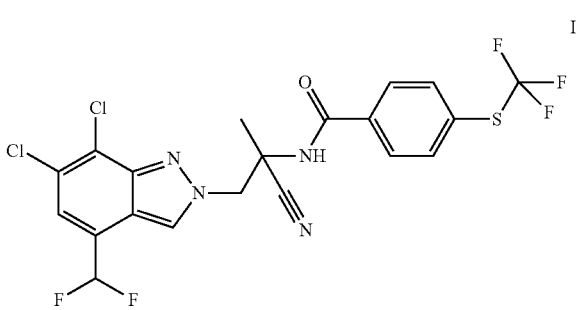 [SMILES: CC(C#N)(Cn1cc2c(C(F)F)cc(Cl)c(Cl)c2n1)NC(=O)c1ccc(SC(F)(F)F)cc1]

and/or an acceptable salt thereof and/or an enantiomer thereof.

2. The compound of claim 1, wherein the compound is enriched in an enantiomer.

3. The compound of claim 2, wherein the compound is enriched in the (R)-enantiomer.

4. The compound of claim 2, wherein the compound is enriched in the (R)-enantiomer in a ratio of at least 95:5 by weight.

5. A parasiticidal composition comprising the compound formula I of claim 1, or salt thereof, and a pharmaceutically acceptable carrier.

6. The composition of claim 5, wherein the composition is formulated for oral administration, topical administration or injectable administration.

7. The composition of claim 5 further comprising one or more additional parasiticidal active agents.

8. The composition of claim 7, wherein the additional parasiticidal active agent is selected from the group consisting of one or more macrocyclic lactones, one or more spinosyn compounds, one or more spinosoid compounds, one or more cyclic depsipeptides, one or more benzimidazoles, levamisole, pyrantel, morantel, praziquantel, closantel, clorsulon, one or more amino acetonitrile active agents, one or more insect growth regulators, one or more pyrethoids, one or more phenylpyrazoles, one or more neonicotinoids and one or more different aryloazol-2-yl cyanoethylamino active agents, or a combination thereof.

9. The composition of claim 8, wherein the additional active agent(s) is a macrocyclic lactone.

10. The composition of claim 9, wherein the macrocyclic lactone is an avermectin or milbemycin selected from the group consisting of abamectin, dimadectin, doramectin, emamectin, eprinomectin, ivermectin, latidectin, lepimectin, selamectin, milbemectin, milbemycin D, milbemycin $A_3$, milbemycin $A_4$, milbemycin oxime, moxidectin and nemadectin.

11. The composition of claim 10, wherein the macrocyclic lactone is ivermectin, eprinomectin, selamectin, milbemycin oxime or moxidectin.

12. The composition of claim 6, wherein the composition is a chewable composition.

13. The composition of claim 6, wherein the composition is an oral drench composition.

14. The composition of claim 6, wherein the composition is a pour-on composition.

15. The composition of claim 6, wherein the composition is a spot-on composition.

16. A method for treating an endoparasitic infection in a mammal which comprises administering an effective amount of the compound of formula I in claim 1, or the parasiticidal composition of claim 5, to the animal.

17. The method of claim 16, wherein the endoparasiticidal infection is caused by an endoparasite selected from the group consisting of Anaplocephaela (*Anoplocephala*), *Ancylostoma, Anecator, Ascaris, Brugia, Bunostomum, Capillaria, Chabertia, Cooperia, Cyathostomum, Cylicocyclus, Cylicodontophorus, Cylicostephanus, Craterostomum, Dictyocaulus, Dipetalonema, Dipylidium, Dirofilaria, Dracunculus, Echinococcus, Enterobius, Fasciola, Filaroides, Habronema, Haemonchus, Metastrongylus, Moniezia, Necator, Nematodirus, Nippostrongylus, Oesophagostumum, Onchocerca, Ostertagia, Oxyuris, Paracaris, Schistosoma, Strongylus, Taenia, Toxocara, Strongyloides, Toxascaris, Trichinella, Trichuris, Trichostrongylus, Triodontophorous, Uncinaria, Wuchereria*, and combinations thereof.

18. The method of claim 17, wherein the endoparasite is *Haemonchus contortus, Ostertagia circumcincta, Trichostrongylus axei, Trichostrongylus colubriformis, Cooperia curticei, Nematodirus battus* or combinations thereof.

19. The method of claim 16, wherein the endoparasite is resistant to avermectin or milbemycin therapy.

* * * * *